United States Patent [19]

Carter et al.

[11] Patent Number: 5,786,282
[45] Date of Patent: Jul. 28, 1998

[54] OPENED WET PROCESSED INTERMEDIATE NATURAL FIBER PRODUCT SUITABLE FOR FORMATION INTO END USE FIBER PRODUCTS WITH LONG-LASTING ANTIMICROBIAL PROPERTIES AND METHOD

[75] Inventors: Larry Dean Carter, Fort Mill, S.C.; Carole Lundberg Reaves, Gastonia, N.C.

[73] Assignee: Barnhardt Manufacturing Company, Charlotte, N.C.

[21] Appl. No.: 806,157

[22] Filed: Feb. 25, 1997

[51] Int. Cl.$^6$ ............................................. B32B 19/00
[52] U.S. Cl. ........................... 442/123; 428/357; 8/181
[58] Field of Search ........................ 428/357; 442/123; 8/181

[56] References Cited

U.S. PATENT DOCUMENTS

| | | | |
|---|---|---|---|
| 4,618,496 | 10/1986 | Brasseur | 424/195.1 |
| 4,692,374 | 9/1987 | Bouchette | 442/327 |
| 4,755,421 | 7/1988 | Manning et al. | 442/338 |
| 4,837,079 | 6/1989 | Quantrille et al. | 442/123 |
| 5,314,719 | 5/1994 | Batdorf et al. | 428/457 |
| 5,585,407 | 12/1996 | Patel et al. | 514/772.6 |
| 5,652,049 | 7/1997 | Suzuki | 442/387 |

OTHER PUBLICATIONS

John D. Payne and D.W. Kudner; *A Durable Antiodor Finish for Cotton Textiles*; vol. 28, No. 5, pp. 28–30; Date and Place of Publication Unknown.

W. Curtis White, *Microbiological Contamination: The Unseen Problem In The Workplace*; pp. 190 & 192; Published Feb. 1996; Place of Publication Unknown.

J.D. Payne and D.W. Kudner; *A New Durable Antimicrobial Finish For Cotton Textiles*; pp. 26–30; Published Jun. 1996; Place of Publication Unknown.

Mr. Runciman and Sandra Luebbecke; *Antibacterial Assessment Report*; pp. "2 and 3"; Published Jul. 2, 1996, Toronto, Ontario, Canada.

Thomson Research Associates; *Technical Data Sheet Ultra-Fresh 40*; All 9 attached pages; Date of Publication Unknown, Toronto, Ontario, Canada.

*Primary Examiner*—Terrel Morris
*Attorney, Agent, or Firm*—Adams Law Firm, P.A.

[57] ABSTRACT

An opened, wet processed, intermediate natural fiber product suitable for formation into end use fiber products, which includes an effective amount of an antimicrobial agent applied to the fibers during wet processing.

10 Claims, No Drawings

OPENED WET PROCESSED INTERMEDIATE NATURAL FIBER PRODUCT SUITABLE FOR FORMATION INTO END USE FIBER PRODUCTS WITH LONG-LASTING ANTIMICROBIAL PROPERTIES AND METHOD

TECHNICAL FIELD AND BACKGROUND OF THE INVENTION

This invention relates to an opened, wet processed, intermediate natural fiber product suitable for formation by downstream processes into end use fiber products, and having long-lasting antimicrobial properties. This application also discloses a method for producing the antimicrobial natural fiber product. The fiber referred to by way of example in this application is cotton, and may include virgin cotton from the gin or mill waste cotton. End uses envisioned for the opened fiber include non-woven products such as swabs and medical/dental cotton bandages, disposable garments and woven and knitted products of any type wherein odor and/or bacterial control is necessary or desirable. The fiber product is referred to as "intermediate" because it has undergone preliminary processing steps through wet processing in open fiber form, and is in a condition to be further processed into a desired end product.

The term "antimicrobial" as used in this application refers to a class of chemicals which kills or interferes with the multiplication, growth or activity of bacteria, fungi or yeasts. Such organisms can cause deterioration of many organic products, staining, putrid and mildew odors, health problems ranging from the stimulation of allergies to irritation and sensitization. The growth of microbes on furniture, clothing, bandages and the like can cause disease as well as promote the spread of the disease. The trend towards laundering clothes in cold or reduced-temperature hot water reduces the ability of laundering to kill contaminated articles.

Odor and microbial control on natural fibers, including cotton is well known. However, present processes apply antimicrobial agents near or at the end of processing. In fabric formation, for example, antimicrobial agents are padded onto the already-formed fabric. In other instances, for example hosiery knitting, the antimicrobial agent is typically applied after the sock is knitted. Cellulose pulp such as used in disposable diapers and sanitary napkins can be sprayed with an antimicrobial agent as a final step in processing.

In contrast with the above, the ability for downstream processors to use cotton which has been previously wet processed with an antimicrobial agent will permit many facilities without wet processing equipment to nevertheless manufacture products having antimicrobial properties.

Other advantages of applying antimicrobial agents during the wet processing steps include the fact that in many applications the presence of the antimicrobial agent on the fiber prior to production of the end use product will enable the manufacturer to avoid further wet processing. This may reduce or eliminate shrinkage or distortion of fabrics and other end use products. In addition, application of the antimicrobial agent to the fiber while the fiber is open and completely saturated may improve penetration of the antimicrobial agent into the fiber and thus provide more even distribution. Applicant has found that satisfactory results can be achieved with add-ons of antimicrobial agents which are substantially less than disclosed in the art as being necessary and reduces the amount of antimicrobial agent needed for a satisfactory application. Applicant has also found that the heat applied to the fibers during drying after application of the antimicrobial agent eliminates the need to "fix" the antimicrobial agent, as is required for some antimicrobial agents.

SUMMARY OF THE INVENTION

Therefore, it is an object of the invention to provide an opened, wet processed, intermediate natural fiber product suitable for formation by downstream processes into end use fiber products with long-lasting antimicrobial properties, and a method for producing the antimicrobial agent natural fiber product.

It is another object of the invention to provide an opened, wet processed, intermediate natural fiber product which provides greater versatility to the fiber product.

It is another object of the invention to provide an opened, wet processed, intermediate natural fiber product which uses less of the antimicrobial agent to achieve satisfactory results.

It is another object of the invention to provide an opened, wet processed, intermediate natural fiber product which achieves satisfactory antimicrobial properties with less add-on.

It is another object of the invention to provide an opened, wet processed, intermediate natural fiber product which does not need a "fixing" treatment after treatment with the antimicrobial agent.

These and other objects of the present invention are achieved in the preferred embodiments disclosed below by providing an opened, wet processed, intermediate natural fiber product suitable for formation into end use fiber products, which comprises an effective amount of an antimicrobial agent applied to the fibers during wet processing.

According to one preferred embodiment of the invention, the opened, wet processed, intermediate natural fiber product includes an effective amount of an antimicrobial agent cationically bonded to the fibers during wet processing.

According to yet another preferred embodiment of the invention, the opened, wet processed, intermediate natural fiber product includes an effective amount of an antimicrobial agent applied to the fibers during wet processing, and chosen from the group consisting of poly (hexamethylenebiguanide) hydrochloride and diiodomethyl-p-tolylsulfone.

According to yet another preferred embodiment of the invention, the opened, wet processed, intermediate natural fiber product comprises a cellulosic fiber.

According to yet another preferred embodiment of the invention, the cellulosic fiber comprises cotton.

According to yet another preferred embodiment of the invention, the poly (hexamethylenebiguanide) hydrochloride is applied to the fiber at a rate of 1.0 percent of the fiber weight.

According to yet another preferred embodiment of the invention, the diiodomethyl-p-tolylsulfone is applied to the fiber at a rate of 0.4 percent of the fiber weight.

An embodiment of the method of imparting antibacterial characteristics to raw natural fiber stock according to the invention comprises the steps of wetting out the fiber stock with a surfactant, conventionally wet processing the fiber stock in a vessel containing one or more aqueous treatment baths; subsequent to the wet processing step applying an effective amount of an antimicrobial agent onto the wet fiber stock, and drying the fiber stock.

According to one preferred embodiment of the invention, the wetting out step includes the step of placing the fiber stock into a treatment basket which in turn is placed into kier.

3

According to another preferred embodiment of the invention, the wet processing step includes processes chosen from the group comprising scouring, bleaching, rinsing, acid neutralizing and finishing steps.

According to yet another preferred embodiment of the invention, the step of applying the antimicrobial agent includes the step of adding the antimicrobial agent into the kier and dispersing the antimicrobial agent evenly throughout the fiber stock.

DESCRIPTION OF THE PREFERRED EMBODIMENT AND BEST MODE

General Description of Wet Processing

A conventional wet process treatment for raw, opened cotton fiber is set out below:

The cotton, for example, 3000 pounds, is wet out with a surfactant as it is compacted into a treatment basket which is then placed in a kier. The kier filled with water and a suitable amount of caustic soda is added. The cotton is thus scoured to remove dirt, grime, oil, vegetable and other foreign matter. The cotton is rinsed and then bleached using a hydrogen peroxide/hot water bath. After a further rinse, the cotton is then neutralized to adjust the pH to within proper limits and again rinsed. Conventionally, a finish application may be applied to the cotton at this point, followed by a final rinse, drying and baling.

Application of Preferred Antimicrobial Agent

In the process according to the invention, after the final rinse and prior to drying, the kier is drained, the kier refilled with water and 30 pounds (one percent of the dry fiber weight) of the antimicrobial agent is added into the bath. The antimicrobial agent is circulated by the water through the fibers for 20 minutes at 125° F. The kier is then drained, the basket removed from the kier and the cotton dried and baled conventionally.

The process described above is a closed bleaching system wherein the raw cotton is fully wet processed in a single series of steps without intermediate drying.

The particular antimicrobial agent used in the above-described example is poly (hexamethylenebiguanide) hydrochloride sold under the trademark Reputex-20 and manufactured by Zeneca Biocides of Wilmington, Del. Reputex-20 is a 20% active solution.

Poly (hexamethylenebiguanide) hydrochloride is particular suited for this use since it has been proven safe for human contact during long use. It shows good antimicrobial activity against a wide spectrum of bacteria, yeasts, and fungi, and has low environmental impact since it contains no heavy metals, formaldehyde, organic halogens or phenolics. It is bioeliminated by adsorption.

The polymeric cationic nature of poly (hexamethylenebiguanide) hydrochloride allows it to bind tightly in an ionic bond to cellulosic materials via an acid-base interaction. The aqueous treatment of cotton, as described above, cause rapid adsorption onto the surface of the fibers. It has been determined that when applied during the wet processing of the open fiber it is not necessary to then treat the fibers with an acidic fixing agent if the fibers are to be utilized in a nondurable end product, for example, medical bandaging. Elevated temperature or curing are not required, although it is believed that the heat applied to the fibers during drying prior to baling causes the agent to bind even more tightly to the binding sites on the surface of the fibers.

4

In situations where the fibers are to be incorporated into fabrics or other durable end products which are intended to be repeatedly laundered, a treatment with an acid fixing agent is desireable. The result is a very durable, long-lasting and stable antimicrobial activity. Because of the ionic binding of this antimicrobial agent with the fibers, this application is particularly suited to uses where repeated laundering or durability are important factors.

It has been found that the use of poly (hexamethylenebiguanide) hydrochloride is particularly effective in end uses where microbes come directly into contact with the treated surface of the fibers for a short duration of time.

Application of Alternate Antimicrobial Agent

Another suitable antimicrobial agent is diiodomethyl-p-tolylsulfone. This antimicrobial agent is sold under the trademark Ultra-Fresh40 or UF40, and is manufactured by Thomson Research Associates of Toronto, Ontario, Canada. Ultra-Fresh40 is a 40% active solution. Diiodomethyl-p-tolylsulfone is a light brown, finely divided, water-based suspension which inhibits the growth of a wide spectrum of bacteria, fungi, molds and mildew. Add-on to the fiber is generally 0.10 percent.

The conventional wet processing steps are the same as set out above.

In the process according to this embodiment of the invention, after the final rinse and prior to drying, the kier is drained, the kier refilled with water and 12 pounds (0.4 percent of the dry fiber weight) of the diiodomethyl-p-tolylsulfone is added into the bath. The antimicrobial agent is circulated by the water through the fibers for 20 minutes at 125° F. The kier is then drained, the basket removed from the kier and the cotton dried and baled conventionally.

The resulting intermediate fiber product is one where the antimicrobial agent is thermoset onto the cotton fibers. Diiodomethyl-p-tolylsulfone has the ability to migrate to the surface of the fibers, thus killing or deactivating microbes which come near the surface of the fiber as well as into contact with the fiber.

Objective Assessment of Antimicrobial Finishes on Textile Materials

The following American Association of Textile Chemists and Colorists (AATCC) tests demonstrate the effectiveness of the open cotton fibers treated with Reputex-20 brand poly (hexamethylenebiguanide) hydrochloride and Ultra-Fresh40 brand of Diiodomethyl-p-tolylsulfone.

TABLE 1

AATCC TEST METHOD 100-1993
LABORATORY TESTING RESULTS - BACTERIA REDUCTION

| | Test Laboratories | | |
|---|---|---|---|
| Treated Sample Description | Thomson Associates | Zeneca Biocides | N. American Science Associates |
| Comber Cotton, 0.2% UF-40 Antimicrobial, Air Dried | — | — | 99.96 PRB* |
| Comber Cotton, 0.2%. UF-40 Antimicrobial, Oven Dried | — | — | — |
| Comber Cotton, 0.4% | — | — | 99.95 PRB |

TABLE 1-continued

AATCC TEST METHOD 100-1993
LABORATORY TESTING RESULTS - BACTERIA REDUCTION

| | Test Laboratories | | |
|---|---|---|---|
| Treated Sample Description | Thomson Associates | Zeneca Biocides | N. American Science Associates |
| UF-40 Antimicrobial, Air Dried Comber Cotton, 0.4% UF-40 Antimicrobial, Oven Dried | — | — | 99.96 PRB |
| High Mic Cotton, 2.0% Reputex 20 Antimicrobial, Inside-Oven Dried | — | 99.72 PRB 99.38 PRB | — |
| High Mic Cotton, 2.0% Reputex 20 Antimicrobial, Outside-Oven Dried | — | 99.52 PRB 99.69 PRB | — |

*PRB - Results indicate a percent reduction of bacteria after being exposed for 24 hours.

TABLE 2

AATCC TEST METHOD 147-1993
LABORATORY TESTING RESULTS - CONTACT INHIBITION (%)

| | Test Laboratories | | |
|---|---|---|---|
| Treated Sample Description | Thomson Associates | Zeneca Biocides | N. American Science Associates |
| Comber Cotton, 0.2% UF-40 Antimicrobial, Air Dried | 100* | — | 0 |
| Comber Cotton, 0.2%. UF-40 Antimicrobial, Oven Dried | 0 | — | — |
| Comber Cotton, 0.4% UF-40 Antimicrobial, Air Dried | 100 | — | 100 |
| Comber Cotton, 0.4% UF-40 Antimicrobial, Oven Dried | 100 | — | 100 |
| High Mic Cotton, 2.0% Reputex 20 Antimicrobial, Inside-Oven Dried | — | — | 0 |
| High Mic Cotton, 2.0% Reputex 20 Antimicrobial, Outside-Oven Dried | — | — | 0 |

*100 - Results indicate percent inhibition of growth under sample.

TABLE 3

AATCC TEST METHOD 147-1993
LABORATORY TESTING RESULTS - GROWTH FREE ZONE (MM)

| | Test Laboratories | | |
|---|---|---|---|
| Treated Sample Description | Thomson Associates | Zeneca Biocides | N. American Science Associates |
| Comber Cotton, 0.2% UF-40 Antimicrobial, Air Dried | 1 mm* | — | 0 |
| Comber Cotton, 0.2% UF-40 Antimicrobial, Oven Dried | 0 | — | — |
| Comber Cotton, 0.4% UF-4 0 Antimicrobial Air Dried | 1 mm | — | 0 |

TABLE 3-continued

AATCC TEST METHOD 147-1993
LABORATORY TESTING RESULTS - GROWTH FREE ZONE (MM)

| | Test Laboratories | | |
|---|---|---|---|
| Treated Sample Description | Thomson Associates | Zeneca Biocides | N. American Science Associates |
| Comber Cotton, 0.4% UF-40 Antimicrobial Oven Dried | 0 | — | 0 |
| High Mic Cotton, 2.0% Reputex 20 Antimicrobial Inside-Oven Dried | — | — | 0 |
| High Mic Cotton, 2.0% Reputex 20 Antimicrobial, Outside-Oven Dried | — | — | 0 |

*1 - All results indicate growth free zone.

TABLE 4

AATCC TEST METHOD 30-1993
LABORATORY TESTING RESULTS - SURFACE INHIBITION (%)

| | Test Laboratories | | |
|---|---|---|---|
| Treated Sample Description | Thomson Associates | Zeneca Biocides | N. American Science Associates |
| Comber Cotton, 0.2% UF-40 Antimicrobial Air Dried | 100* | — | 0** 0 |
| Comber Cotton, 0.2% UF-4 0 Antimicrobial, Oven Dried | 90 | — | — |
| Comber Cotton, 0.4% UF-40 Antimicrobial, Air Dried | 100 | — | 0 0 |
| Combers Cotton, 0.4% UF-40 Antimicrobial, Oven Dried | 100 | — | 0 0 |
| High Mic Cotton, 2.0% Reputex 20 Antimicrobial, Inside-Oven Dried | — | — | 2*** 2 |
| High Mic Cotton, 2.0% Reputex 20 Antimicrobial, Outside-Oven Dried | — | — | 2 2 |

*100 - Reported as % Surface Inhibition.
**0 - Reported as zero growth. Thus, 0 and 100 in this case imply same.
***2 - Indicates growth on sample; zero does not.

TABLE 5

AATCC TEST METHOD 30-1993
LABORATORY TESTING RESULTS - GROWTH FREE ZONE (MM)

| | Test Laboratories | | |
|---|---|---|---|
| Treated Sample Description | Thomson Associates | Zeneca Biocides | N. American Science Associates |
| Comber Cotton, 0.2% UF-40 Antimicrobial, Air Dried | 0 mm | — | 5 mm* 5 mm |
| Comber Cotton, 0.2% UF-40 Antimicrobial, Oven Dried | 0 mm | — | — |
| Comber Cotton, 0.4% UF-40 Antimicrobial, Air Dried | 6 mm | — | 9 mm 10 mm |
| Comber Cotton, 0.4% | 6 mm | — | 10 mm |

TABLE 5-continued

AATCC TEST METHOD 30-1993
LABORATORY TESTING RESULTS - GROWTH FREE ZONE (MM)

| Treated Sample Description | Test Laboratories | | |
|---|---|---|---|
| | Thomson Associates | Zeneca Biocides | N. American Science Associates |
| UF-40 Antimicrobial, Oven Dried | | | 8 mm |
| High Mic Cotton, 2.0% Reputex 20 Antimicrobial, Inside-Oven Dried | — | — | NZ** NZ |
| High Mic Cotton, 2.0% Reputex 20 Antimicrobial, Outside-Oven Dried | — | — | NZ NZ |

*0 - All numerical results indicate area around sample where no growth occurs.
**NZ - Indicates no growth free zone.

TABLE 6

USP TESTING

| Test Method | 0.2% UF-40 Trial #1 4/18/96 | 0.4% UF-40 Trial #2 5/7/96 | 1% Reputex 20 Trial #5 7/26/96 |
|---|---|---|---|
| Ether Extraction (NMT 0.7%) | 0.22 | 0.15 | 0.14 |
| Water Solubles (NMT 0.35%) | 0.14 | 0.12 | 0.07 |
| Ash Content (NMT 0.20%) | 0.06 | 0.09 | 0.05 |
| pH of Water Extraction (4.4-8.3) | 7.83 | 5.98 | 6.74 |
| Absorbency - S | 22.7 | 23.1 | 23.7 |
| Capacity - NS (NLT 20x) | 23.9 | 22.0 | 24.8 |
| Absorbency Rate - S (NLT 7.0 sec.) - NS | 4.0 4.1 | 4.3 4.4 | 6.4 5.9 |
| Color - L* - S NS | 93.94 94.69 | 94.06 95.02 | 95.99 95.72 |
| b* - S NS | 3.77 2.79 | 3.34 2.22 | 3.20 2.03 |
| (per customer spec) | | | |

An opened, wet processed, intermediate natural fiber product suitable for formation by downstream processes into end use fiber products, and having long-lasting antimicrobial properties is described above. Various details of the invention may be changed without departing from its scope. Furthermore, the foregoing description of the preferred embodiment of the invention and the best mode for practicing the invention are provided for the purpose of illustration only and not for the purpose of limitation-the invention being defined by the claims.

We claim:

1. An opened, wet processed, intermediate dry natural fiber mass having an effective amount of a uniformly dispensed antimicrobial agent thereon, wherein said antimicrobial agent is applied to the fiber mass while the fiber mass is in open form during wet processing and before the fiber mass is dried.

2. An opened, wet processed, intermediate dry natural fiber mass, having an effective amount of a uniformly dispersed antimicrobial agent thereon, wherein said antimicrobial agent is applied to the fiber mass while the fiber mass is in open form during wet processing and is cationically bonded to the fibers of the fiber mass before the fiber mass is dried.

3. An opened, wet processed, intermediate natural dry fiber mass, having an effective amount of a uniformly dispersed antimicrobial agent thereon, wherein said antimicrobial agent is applied to the fiber mass while the fiber mass is in open form during wet processing before the fiber mass is dried, wherein said antimicrobial agent is chosen from the group consisting of poly (hexamethylenebiguanide) hydrochloride and diiodomethyl-p-tolylsulfone.

4. An opened, wet processed, intermediate natural dry fiber mass according to claim 1, 2 or 3, wherein said natural fiber mass comprises cellulosic fibers.

5. An opened, wet processed, intermediate natural dry fiber product according to claim 4 wherein said cellulosic fibers comprise cotton.

6. An opened, wet processed, intermediate natural dry fiber product according to claim 3, wherein said poly (hexamethylenebiguanide) hydrochloride is applied to said fiber mass at a rate of 1.0 percent of the fiber weight.

7. An opened, wet processed, intermediate natural dry fiber product according to claim 3, wherein said diiodomethyl-p-tolylsulfone is applied to said fiber mass at a rate of 0.4 percent of the fiber weight.

8. A method of imparting antibacterial characteristics to opened raw natural fiber stock, comprising the steps of:

(a) wet processing the fiber stock, which wet processing includes the steps of:
  (1) wetting out the fiber stock with a surfactant;
  (2) scouring the fiber stock to remove dirt, oil and foreign matter, and;
  (3) bleaching the fiber stock;

(b) subsequent to bleaching the fiber stock, uniformly applying an effective amount of an antimicrobial agent onto the wet fiber stock; and (c) drying the fiber stock to provide a dry fiber mass having an effective amount of a uniformly dispersed antimicrobial agent thereon.

9. A method according to claim 8, wherein said natural fiber stock comprises cotton.

10. A method according to claim 9, wherein said wetting out step includes the step of placing the fiber stock into a treatment basket which in turn is placed into kier.

* * * * *